United States Patent [19]  
Shalaby et al.

[11] 4,441,496  
[45] Apr. 10, 1984

[54] COPOLYMERS OF P-DIOXANONE AND 2,5-MORPHOLINEDIONES AND SURGICAL DEVICES FORMED THEREFROM HAVING ACCELERATED ABSORPTION CHARACTERISTICS

[75] Inventors: Shalaby W. Shalaby; Donald F. Koelmel, both of Lebanon, N.J.

[73] Assignee: Ethicon, Inc., Somerville, N.J.

[21] Appl. No.: 346,809

[22] Filed: Feb. 8, 1982

[51] Int. Cl.$^3$ .......................... A61L 17/00; A61F 1/24
[52] U.S. Cl. .................................. 128/335.5; 528/354
[58] Field of Search ............. 128/335.5, 92 G; 3/1 B; 528/354, 367

[56] References Cited

U.S. PATENT DOCUMENTS

| | | | |
|---|---|---|---|
| 3,020,289 | 2/1962 | Welpert | 260/340.2 |
| 3,063,967 | 11/1962 | Schultz | 260/78.3 |
| 3,063,968 | 11/1962 | Schultz | 260/78.3 |
| 3,190,858 | 6/1965 | Cox et al. | 260/78.3 |
| 3,391,126 | 7/1968 | Baggett | 528/354 |
| 3,645,941 | 2/1972 | Snapp et al. | 260/18 |
| 3,883,901 | 5/1975 | Coquard | 128/335.5 |
| 3,960,152 | 6/1976 | Augurt | 128/335.5 |
| 4,032,993 | 7/1977 | Coquard | 128/335.5 |
| 4,052,988 | 10/1977 | Doddi et al. | 128/335.5 |
| 4,300,565 | 11/1981 | Rosensaft | 128/335.5 |
| 4,343,931 | 8/1982 | Barrows | 128/335.5 |

FOREIGN PATENT DOCUMENTS 30822 5/1981 European Pat. Off. .

OTHER PUBLICATIONS

Scientific Lib. Computer Search, 08/29/83, DARC System for Substructural Search.
Nissen, D., Gilon, C. & Goodman, M., 1975, Macromol. Chem., Suppl. 1,23.
Mathias, L. J., Fuller, W. D., Missen, D. and Goodman, M., 1978, Macromolecule 11, 534.
Ingwall, R. T. & Goodman, M., 1974, Macromolecules 7, 598.
Ingwall, R. T., Gilon, C. & Goodman, M., 1976, Micromolecules 9, 802.
Ingwall, R. T., 1978, Macromolecules 11, 540.

*Primary Examiner*—C. Fred Rosenbaum
*Assistant Examiner*—Gene Kartchner
*Attorney, Agent, or Firm*—Leonard Kean

[57] ABSTRACT

A copolymer of p-dioxanone and an unsubstituted or loweralkyl substituted 2,5-morpholinedione especially suited for absorbable surgical sutures and other surgical devices having accelerated absorption characteristics, but retaining good tensile strength and a high level of flexibility and softness.

18 Claims, No Drawings

COPOLYMERS OF P-DIOXANONE AND 2,5-MORPHOLINEDIONES AND SURGICAL DEVICES FORMED THEREFROM HAVING ACCELERATED ABSORPTION CHARACTERISTICS

BACKGROUND OF THE INVENTION

This invention relates to copolymers of p-dioxanone and 2,5-morpholinediones and surgical devices formed therefrom, having accelerated absorption characteristics.

Absorbable surgical devices, including suture materials have traditionally been natural collagenous materials obtained from sheep or beef intestine, commonly known as catgut. More recently, it has been proposed to manufacture synthetic absorbable sutures from polyesters of hydroxycarboxylic acids, notably polylactide, polyglycolide, and copolymers of lactide and glycolide. Such synthetic absorbable sutures are described in U.S. Pat. Nos. 3,636,956, 3,297,033 and elsewhere in the literature.

Among the requirements of an ideal absorbable suture are that it should have good handling properties, should approximate and hold tissue for proper healing with minimal tearing and tissue damage, should have adequate straight tensile and knot strength, should be controllably uniform in properties including dimensional stability within the body, should be sterilizable, should be absorbable by living tissue, preferably at a constant rate regardless of the place in the body or the condition of the patient, without causing such unfavorable tissue reactions as walling off, granuloma formation, excessive edema, etc., and finally should be capable of being properly and easily tied into surgical knots.

While multifilament sutures manufactured from polymers of lactide and glycolide fulfill the above requirements to a large degree, monofilament sutures of these materials are considerably less flexible than catgut and these synthetic sutures are accordingly generally limited to a multifilament, braided construction.

In U.S. Pat. No. 4,052,988 there is described polymers of p-dioxanone and 1,4-dioxepan-2-one which can be melt extruded into pliable, monofilament fibers which are slowly absorbed in animal tissue without significant adverse tissue reaction and which have good tensile and knot strength and good in vivo strength retention. However, the absorption characteristics of said polymers are not as fast as would be desirable for certain purposes.

Although U.S. Pat. Nos. 3,063,967 and 3,063,968 describe the polymerization of p-dioxanone and the preparation of films and fibers therefrom, the low tensile strength of fibers prepared in accordance with the teachings of the latter two references, however, make these fibers generally unsuitable for use as surgical sutures. Moreover, there was no appreciation in said latter two references of the absorbability of such fibers which were reported to be resistant to the effects of saline and distilled water.

Other references dealing with the polymerization of p-dioxanone include, but are not limited to, U.S. Pat. Nos. 3,190,858, 3,391,126 and 3,645,941 which disclose various catalysts for the polymerization of lactones such as p-dioxanone, and U.S. Pat. No. 3,020,289 which describes the polymerization of p-dioxanone in the presence of sulfuric acid. None of these references suggest polymers of p-dioxanone for use in the preparation of synthetic absorbable sutures. M. Goodman and his co-workers (see the eight references listed below) prepared several polydepsipeptides (copolymers with repeat units originating from separate derivatives of α-amino and α-hydroxy acids) by the copolymerization of the appropriate cyclic anhydrides of these monomers. Available data do not suggest that these investigators were able to prepare alternating type polydepsipeptides by this route or the direct homopolymerization of the cyclic codimers morpholinediones to form truly regular polydepsipeptides with alternating peptide and ester repeat units. These were never alluded to in any of Goodman's reports. This may be attributed to their inability to prepare morpholine-2,5-diones which are polymerizable to alternating polydepsipeptides. The polydepsipeptides reported by Goodman et al. in U.S. Pat. No. 3,773,737 were described as hydrolytically more stable and hence are less absorbable than polylactides, polyglycolide or polydioxanone.

1. Nissen, D., Gilon, C. and Goodman, M, 1975, Macromol. Chem., Suppl. 1, 23.
2. Mathias, L., J, Fuller, W. D., Nissen, D. and Goodman, M., 1978, Macromolecules 11, 534.
3. Ingwall, R. T. and Goodman, M., 1974, Macromolecules 7, 598.
4. Ingwall, R. T., Gilon, C. and Goodman, M., 1976, Macromolecules 9, 802.
5. Ingwall, R. T., 1978, Macromolecules 11, 540.
6. Goodman, M., Gilon, C., Palumbo, M. and Ingwall, R. T., 1974, Isr. J. Chem. 12, 67.
7. Goodman, M., Gilon, C., and Kirshenbaum, G. S. and Knobler, Y., 1972, Isr. J. Chem. 10,867.
8. Goodman, M., and Kirshenbaum, G. S., (1973) U.S. Pat. No. 3,773,737.

We have discovered that the rate of absorption of polydioxanone such as that disclosed in U.S. Pat. No. 4,052,988, may be enhanced by incorporating 1–15 mole percent of 2,5-morpholinedione or its alkyl substituted derivatives in the chain as a comonomer without adversely affecting the breaking strength retention profiles of the unmodified homopolymer. Furthermore, contrary to what would be expected from the general teachings of Goodman et al. in U.S. Pat. No. 3,773,737, the present copolymer displays a much lower hydrolytic stability as compared to the polydioxanone of U.S. Pat. No. 4,052,988.

SUMMARY

The present invention relates to a copolymer comprising a multiplicity of recurring A and B units having the following general formula:

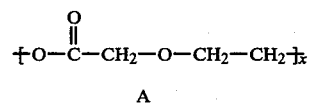

A

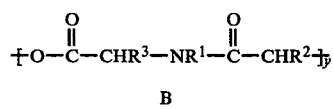

B wherein x and y are integers, such that the A units comprise 85–99 mole percent, and the B units comprise 1–15 mole percent of the copolymer and $R^1$, $R^2$ and $R^3$ are each hydrogen or lower alkyl and may be the same or different.

In accordance with a preferred embodiment of the invention, each of $R^1$, $R^2$ and $R^3$ is hydrogen and the A units comprise 94–98 mole percent and the B units comprise 2–6 mole percent of the copolymer. (Most preferably, the A units comprise 95–97 mole percent, and the B units comprise 3–5 mole percent of the copolymer.)

The invention also comprises absorbable surgical devices (especially sutures and clips) formed from the copolymer.

Within the scope of the present invention is a suture as described having a surgical needle attached to at least one end. Also within the scope of the present invention is such surgical suture in a sterile condition, packaged in a sterile enclosure. Also within the scope of the present invention is a method of closing a wound by approximating and securing the wound tissue with a suture of the present invention.

As may be seen from attached Table I, the copolymers of the present invention may be melt extruded into filaments suitable for use as synthetic absorbable sutures which are characterized by (a) a high level of crystallinity (30–37%), (b) a straight tensile strength of up to 67,000 psi, without any attempt to optimize processing conditions for improved tensile properties, (c) a 96 to 97 percent absorption in buffer at 50° C. after 37 days [in comparison, the polydioxanone control "absorbs" completely at 51 days], (d) higher in vivo absorption than the polydioxanone control itself (virtually complete absorption in 90–150 days versus 182 days for polydioxanone), and (e) excellent in vivo strength retention, as high as 58 and 43 percent in 21 and 28 days, respectively.

DESCRIPTION OF PREFERRED EMBODIMENTS

The copolymers of the present invention are prepared by copolymerizing p-dioxanone having the formula

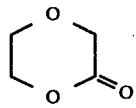

with a 2,5-morpholinedione having the formula

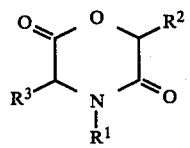

wherein $R^1$, $R^2$ and $R^3$ are each hydrogen or lower alkyl and may be the same or different.

It should be noted that high purity of the p-dioxanone monomer is desirable to obtain copolymers having a sufficiently high inherent viscosity to yield strong fibers upon extrusion. In general, the monomers are purified to 99+ percent by distillation and/or recrystallization prior to polymerization, and the resulting copolymers have an inherent viscosity of at least about 0.50, and preferably 1.1 or higher. As set forth in Tables I and II, copolymers prepared from highly purified dioxanone have inherent viscosities well in excess of 1.10.

The p-dioxanone monomer is conveniently prepared by reacting diethylene glycol, metallic sodium, and chloroacetic acid, as described in U.S. Pat. No. 4,052,988. The 2,5-morpholinedione monomer may be prepared by heating, in vacuum, the dry salt formed upon neutralizing N-(bromoacetyl)-glycine with sodium hydroxide. To produce the N-(bromoacetyl)-glycine, a mixture of glycine in tetrahydrofuran is condensed with bromoacetyl bromide. The 3-methyl-2,5-morpholinedione monomer is prepared in a similar manner by substituting N-(chloroacetyl)-L-alanine in place of the N-(bromoacetyl)-glycine. The N-methyl-2,5-morpholinedione monomer is prepared by reacting bromoacetyl bromide with sarcosine in the presence of triethylamine, also as described in detail hereinafter.

The copolymer is prepared by polymerizing the two monomers in the presence of an organometallic catalyst such as dibutyl tin oxide diethylzinc, zirconium acetylacetonate or stannous octoate, the latter being preferred.

The monomers, in the desired proportions, are heated in a flame and vacuum dried, sealed glass ampoule according to the following temperature/time scheme:

120°–130° C./1–2 minutes
90°–120° C./1.5–16.5 hours
80°–85° C./23.5 hours–120 hours The resulting copolymer is isolated and ground after chilling in liquid nitrogen. The copolymer chips are first dried under vacuum and then devolatilized. The devolatilized copolymer is then formed into surgical devices, such as filaments.

In order to prepare such filaments, the copolymer is melt extruded through a spinneret in a conventional manner to form one or more filaments which are subsequently drawn about 4× to 6× in order to achieve molecular orientation and improve tensile properties. The resulting oriented filaments have good tensile and dry knot strength and good in vivo strength retention, as well as accelerated absorption characteristics.

To further improve dimensional stability and tensile strength retention, the oriented filaments may be subjected to an annealing treatment. This optional annealing treatment consists of heating the filaments to a temperature of from about 50° to 95° C., most preferably from about 50° to 80° C. while restraining the filaments to prevent any substantial shrinkage. The filaments are held at the annealing temperature for a few seconds to several days or longer depending on the temperature and processing conditions. In general, annealing at 50° to 80° C. for up to about 24 hours is satisfactory. Optimum annealing time and temperature for maximum improvement in fiber in vivo strength retention and dimensional stability is readily determined for each fiber composition.

Since the function of a suture is to join and hold severed tissue until healing is well along, and to prevent separation as a result of movement or exercise, a suture must meet certain minimum standards of strength. It is particularly important that strength be maintained when knots are tied and during the actual procedure of drawing tight a suitable knot. Oriented filaments of the present invention possess a straight tensile strength of at least about 36,000 psi and a knot strength of at least about 30,000 psi, although significantly higher strengths are possible as will be apparent from Tables I and II.

The preparation of the copolymers of the present invention is illustrate by the following examples.

EXAMPLE 1

Preparation of N-(bromoacetyl)-glycine

The preparation of this compound is patterned after the synthesis of similar compounds as described by A. H. Cook and G. F. Cox in the Journal of the Chemical Society, 2347-2351, 1949. The synthetic procedure used to make N-(bromoacetyl)-glycine is as follows: A fine powder of glycine (300 g, 4.0 moles) is suspended in dry THF (tetrahydrofuran) (2600 ml). A solution of bromoacetyl bromide (404 g, 2.0 moles) in dry THF (1200 ml) is slowly added to the mechanically stirred glycine suspension. After 4 to 5 hours of stirring at room temperature, the reaction mixture is filtered. The filtrate is placed on a rotary evaporator and the THF distilled off. THF evaporation produces a yellow oil which crystallizes upon standing at room temperature. Recrystallization of this solid from ethyl acetate produces 133 g of N-(bromoacetyl)-glycine (m.p.=114°-116° C.) An infrared spectrum of this purified compound shows a broad N-H stretching band from 3260 to 3400 $cm^{-1}$ and from 3020 to 3080 $cm^{-1}$, a sharp acid carbonyl absorption band at 1730 $cm^{-1}$, a broad split amide carbonyl absorption band from 1640 to 1660 $cm^{-1}$, and a sharp N-H bending band at 1540 $cm^{-1}$.

EXAMPLE 2

Preparation of 2,5-Morpholinedione

A pure sample (m.p. 113°-115° C.) of N-(bromoacetyl)-glycine (131.2 g, 0.67 moles), prepared in accordance with Example 1, is dissolved in 650 ml of tetrahydrofuran at room temperature. Then 134 ml (0.67 moles) of a 5 N NaOH solution are slowly added to the THF solution with vigorous stirring at room temperature. After 4 hours of stirring at room temperature the aqueous phase is separated from the THF layer with a separatory funnel. In vacuo evaporation of the aqueous phase produces 125.4 g of the sodium salt of N-(bromoacetyl)-glycine. After thorough drying at 90° C. under vacuum, this salt is mixed with an equivalent weight of sand, placed in a large sublimating apparatus and heated under vacuum (<0.1 mm) at 180° C. and 200° C. for 24 and 16 hours, respectively.

A yellow sublimate (11.5 g) is collected and subsequently recrystallized three times from boiling $CH_3CN$ to yield (4 g) 2,5-morpholinedione (m.p. 194°-196° C.). The I.R. spectrum of this material shows a sharp lactone carbonyl absorption band at 1755 $cm^{-1}$, a sharp lactam carbonyl absorption band at 1700 $cm^{-1}$, and a small N-H bending band at 1550 $cm^{-1}$. Proton NMR analysis of this compound shows chemical shifts at 4.69, 4.06 and 4.03 PPM. A mass spectral analysis of the compound indicates a molecular ion of 115 M/e.

Elemental Analysis—Calculated for $C_4H_5NO_3$: C, 41.74; H, 4.38; N, 12.17; O, 41.70%. Found: C, 41.94; H, 4.08; N, 11.98; O, 41.88%

EXAMPLE 3

Preparation of N-Methyl-2,5-Morpholinedione

Bromacetyl bromide (202 g, 1.0 moles) is dissolved in THF (400 ml) and rapidly added to a cooled (15° C.), vigorously stirred sarcosine (178.2, 2.0 moles)-THF (900 ml) mixture. After two hours of thorough mixing at room temperature the reaction mixture is filtered. Triethylamine (101 g, 1.0 moles) is added to the filtrate. This reaction mixture is stirred at 50° C. for 0.25 hours and then filtered. Evaporation of this filtrate's solvent produces roughly 80 g of crude, liquid N-methyl-2,5-morpholinedione. Vacuum distillation of this oil yields 60 g of N-methyl-2,5-morpholinedione (B.P. 114°-116° C. at 0.1 mm, $N_D^{23}$=1.4967). Proton NMR analysis of the distillate shows chemical shifts at 2.952, 2.985, 3.94, 4.16, and 4.74 PPM. Elemental analysis of the compound is as follows—calculated for $C_5H_7NO_3$: C, 46.50; H, 5.48; N, 10.84; O, 37.17%. Found: C, 46.78; H, 5.80; N, 11.16; O, 36.47%.

EXAMPLE 4

Preparation of 3-Methyl-2,5-Morpholinedione

A pure sample (m.p. 93°-95° C.) of N-(chloroacetyl)-L-alanine (22.4 g, 0.13 moles), made under similar conditions to those described in Example 1, was dissolved in 100 ml of tetrahydrofuran at room temperature. Then, 27 ml (0.13 moles) of a 5 N NaOH solution were slowly added to the THF solution with vigorous stirring at room temperature. After 4 hours of stirring at room temperature the aqueous phase was separated from the THF layer with a separatory funnel. In vacuo evaporation of the aqueous phase produced 21.6 g of the sodium salt of N-(chloroacetyl)-L-alanine. After thorough drying at 90° C. under vacuum, this salt was mixed with an equivalent weight of sand, placed in a small sublimating apparatus and heated under vacuum (<0.1 mm) at 150° C., 160° C. and 170° C. for 40, 42 and 18 hours, respectively.

A yellow sublimate (2.4 g) was collected and subsequently recrystallized three times from boiling $CH_3CN$ to yield (1.0 g) 3-methyl-2,5-morpholinedione (m.p. 139°-141° C.). Proton NMR analysis of this compound shows a doublet between 0.97 and 1.042 PPM, a quartet between 3.310 and 3.390 PPM, and second order splitting between 4.223 and 4.250 PPM.

EXAMPLE 5

99/1 p-Dioxanone/2,5-Morpholinedione Copolymer p-Dioxanone (87.8 g, 0.861 moles), 2,5-morpholinedione (1.0 g, 0.0087 moles), 1-dodecanol (0.27 g, 0.00145 moles) and a catalytic amount of stannous octoate (0.176 ml of 0.33 M toluene solution, 0.000058 moles) are heated and magnetically mixed in a flame and vacuum dried, sealed glass ampoule according to the following temperature/time scheme:

120° C./1 minute
90° C./2.5 hours
80° C./112 hours

The resulting copolymer is isolated and ground after chilling in liquid nitrogen. The copolymer chips are first dried under vacuum (<0.1 mm) at room temperature for 16 hours and then devolatilized at 87° C. and 0.05 mm pressure for 16 hours. The devolatilized copolymer sample is then melt spun into monofilaments.

EXAMPLE 6 (Sample V-P)

97/3 -p-Dioxanone/2,5-Morpholinedione Copolymer p-Dioxanone (20.1 g, 0.197 moles), 2,5-morpholinedione (0.7 g, 0.00609 moles), 1-dodecanol (0.0623 g, 0.000334 moles), and a catalytic amount of stannous octoate (0.51 ml of a 0.0264 M toluene solution, 0.0000135 moles) are heated and magnetically mixed in a flame and vacuum dried, sealed glass ampoule according to the following temperature/time scheme:

120° C./1 minute

90° C./2.5 hours
80° C./112 hours

The resulting copolymer is isolated and ground after chilling in liquid nitrogen. The copolymer chips are first dried under vacuum (<0.1 mm) at room temperature for 16 hours and then devolatized at 55° C. and 0.05 mm pressure for 16 hours. The devolatilized copolymer sample is then melt spun into monofilaments. (See Table I for monofilament properties.)

EXAMPLE 7 (Sample VI-P)

96/4 p-Dioxanone/2,5-Morpholinedione Copolymer

P-Dioxanone (255.4 g, 2.504 moles), 2,5-morpholinedione (12.0 g, 0.104 moles), 1-dodecanol (0.763 g, 0.00409 moles) and a catalytic amount of stannous octoate (0.525 ml of a 0.33 M toluene solution, 0.000173 moles) are heated and magnetically mixed in a flame and vacuum dried, sealed glass ampoule according to the following temperature/time scheme:
120° C./1 minute
90° C./1.5 hours
85° C./16 hours
80° C./120 hours The resulting copolymer is isolated and ground after chilling in liquid nitrogen. The copolymer chips are first dried under vacuum (<0.1 mm) at room temperature for 16 hours and then devolatilized at 87° C. and 0.05 mm pressure for 16 hours. The devolatilized copolymer sample is then melt spun into monofilaments. (See Table I for monofilament properties.)

Example 8 (Sample IV-P)

95/5 p-Dioxanone/2,5-Morpholinedione copolymer p-Dioxanone (17.7 g, 0.174 moles), 2,5-morpholinedione (1.0 g, 0.00870 moles), 1-dodecanol (0.558 g, 0.000299 moles), and a catalytic amount of stannous octoate (0.46 ml of a 0.0264 M toluene solution, 0.000021 moles) are heated and magnetically mixed in a flame and vacuum dried, sealed glass ampoule according to the following temperature/time scheme:
120° C./1 minute
90° C./2.5 hours
80° C./112 hours The resulting copolymer is isolated and ground after chilling in liquid nitrogen. The copolymer chips are first dried under vacuum (<0.1 mm) at room temperature for 16 hours and then devolatilized at 55° C. and 0.05 mm pressure for 16 hours. The devolatilized copolymer sample is then melt spun into monofilaments. (See Table I for monofilament properties.)

EXAMPLE 9 (Sample 1-P)

90/10 p-Dioxanone/2,5-Morpholinedione copolymer p-Dioxanone (4.0 g, 0.039 moles), 2,5-morpholinedione (0.5 g, 0.0043 moles) and a catalytic amount of stannous octoate (0.22 ml of a 0.0132 M toluene solution, 0.0000029 moles) are heated and magnetically mixed in a flame and vacuum dried, sealed glass ampoule according to the following temperature/time scheme:
130° C./2 minutes
120° C./16.5 hours
80° C./23.5 hours The resulting copolymer is isolated and ground after chilling in liquid nitrogen. The copolymer chips are first dried under vacuum (<0.1 mm) at room temperature for 16 hours and then devolatilized at 50° C. and 0.05 mm pressure for 24 hours. The devolatilized copolymer sample is then melt spun into monofilaments. (See Table I for monofilament properties.)

EXAMPLE 10 (Sample VIII-P)

97/3 p-Dioxanone/3-Methyl-2,5-Morpholinedione Copolymer p-Dioxanone (12.8 g, 0.125 moles), 3-methyl-2,5-morpholinedione (0.5 g, 0.00388 moles), 1-dodecanol (0.0369 g, 0.000198 moles), and a catalytic amount of stannous octoate (0.025 ml of a 0.33 M toluene solution, 0.0000083 moles) are heated and magnetically mixed in a flame and vacuum dried, sealed glass ampoule according to the following temperature/time scheme:
125° C./1 minute
90° C./3.0 hours
80° C./85.5 hours The resulting copolymer is isolated and ground after chilling in liquid nitrogen. The copolymer chips are first dried under vacuum (<0.1 mm) at room temperature for 16 hours and then devolatilized at 80° C. and 0.05 mm pressure for 16 hours. The devolatilized copolymer sample is then melt spun into monofilaments. (See Table II for monofilament properties.)

EXAMPLE 11

96/4 p-Dioxanone/N-Methyl-2,5-Morpholinedione Copolymer p-Dioxanone (28.5 g, 0.279 moles), N-methyl-2,5-morpholinedione (1.5 g, 0.01162 moles), 1-dodecanol (0.082 g, 0.00044 moles), and a catalytic amount of stannous octoate (0.06 ml of a 0.33 M toluene solution, 0.0000198 moles) are heated and magnetically mixed in a flame and vacuum dried, sealed glass ampule according to the following temperature/time scheme:
90° C./3.0 hours
80° C./111.5 hours The resulting copolymer is isolated and ground after chilling in liquid nitrogen. The copolymer chips are first dried under vacuum (<0.1 mm) at room temperature for 16 hours and then devolatilized at 85° C. and 0.05 mm pressure for 16 hours.

The $T_m$ of the product is 103°–108° C., and the I.V. in H.F.I.P. at 25° C. is 1.08.

EXAMPLE 12 (Sample VII-P)

Poly p-Dioxanone: Control Sample p-Dioxanone (20.0 g, 0.196 moles), 1-dodecanol (0.0574 g, 0.000308 moles) and a catalytic amount of stannous octoate (0.495 ml of a 0.0264 M toluene solution, 0.0000131 moles) are heated and magnetically mixed in a flame and vacuum dried, sealed ampoule according to the following temperature/time scheme:
120° C./1 minute
90° C./2.5 hours
80° C./112 hours The resulting polymer is isolated and ground after chilling in liquid nitrogen. The polymer chips are first dried under vacuum (<0.1 mm) at room temperature for 16 hours and then devolatilized at 55° C. and 0.05 mm pressure for 16 hours. The devolatized polymer sample is then melt spun into monofilaments. (See Table I for monofilament properties.)

TABLE I

PHYSICAL PROPERTIES, in vitro and in vivo BEHAVIOR OF MONOFILAMENTS MADE FROM PDO/MD COPOLYMERS

| Sample No. | PDO/MD | Fiber IV | $T_m$ °C. | % Cryst. | Anneal. °C./hr. | Str. Stren. psi | Knot Stren. psi | % Elong. | in vitro Abs. (50° C.) % Rem./Days | in vivo BSR % Rem./Days | in vivo Abs. % Rem./Days |
|---|---|---|---|---|---|---|---|---|---|---|---|
| I-P | 90/10 | | | | None | | | | .4/19 | Not Tested | Not Tested |
| II-P | 95/5 | 1.38 | 99.5 | | None | 36,500 | 31,500 | 41.5 | 1.8/18 | 1.27 lb. Init. 64/7 39/14 0/28 | 100/5 100/31 67.5/60 0/90 |
| III-P | 97/3 | 1.18 | | | None | 37,000 | 32,000 | 54 | 11.7/18 | Not Tested | Not Tested |
| IV-P | 95/5 | 1.50 | | 30 | None | 62,000 | 45,000 | 58 | 5.4/28 | 2.84 lb. Init. 71/7 61/14 47/21 23/28 | 100/5 84/63 0/120 |
| IV-P | 95/5 | 1.49 | 96 | 35 | 77/24 | 61,000 | N.T. | 62 | 5.3/28 | 2.89 lb. Init. 85/7 74/14 58/21 43/28 | 100/5 77/63 87.5/90 0/120 |
| V-P | 97/3 | 1.50 | 100 | 32 | None | 64,000 | 38,000 | 51 | 2.9/37 | 2.88 lb. Init. 86/7 66/14 56/21 | 100/5 88/63 5.5/120 0/150 |
| V-P | 97/3 | 1.51 | | 34 | 77/24 | 67,000 | N.T. | 45 | 3.9/37 | 2.85 lb. Init. 81/7 73/14 49/28 | 100/5 91/63 46.5/120 0/150 |
| VI-P | 96/4 | 1.60 | | | None | 58,000 | 40,000 | 60 | 2.38/32 | Not Tested | Not Tested |
| VI-P | 96/4 | 1.60 | | 37 | 78/24 | 68,000 | 43,500 | 62 | | 2.66 lb. Init. 70/14 59/21 | 100/5 100/14 95/90 0/120 |
| VII-P | PDS (Control) | 1.38 | | | 80/24 | 71,000 | 50,000 | 37 | 6.4/45 1.9/51 2.7/45* 1.6/51* | 3.29 lb. Init. 86.9/7 72.8/14 59.9/21 49.6/28 | 100/7 100/14 86/63 74/91 81/118 52.5/150 0/182 |

*Unannealed

TABLE II

PHYSICAL PROPERTIES, in vitro and in vivo BEHAVIOR OF MONOFILAMENTS MADE FROM PDO/3MMD COPOLYMERS

| Sample No. | PDO/ 3MMD | Fiber IV | $T_m$ °C. | % Cryst. | Anneal. °C./hr. | Straight Strength (psi) | Knot Strength (psi) | % Elong. | in vitro Abs. 50° C. % Rem./Days | in vivo BSR % Rem./Days | in vivo Abs. % Rem./Days |
|---|---|---|---|---|---|---|---|---|---|---|---|
| VIIIP | 97/3 | 1.59 | 103 | — | None | 58,900 | 36,400 | 88 | 2.1/29 0.5/32 | Not Tested | Not Tested |
| VIIIP | 97/3 | 1.59 | 103 | 30 | 82/24 | — | — | — | 6.6/29 0.3/32 | 3.07 Init. 72.9/7 58.9/14 42.7/28 | 100/5 100/63 64.5/120 0/150 |

In Tables I and II, the abbreviations used, have the following significance (all percentages being in weight):

| | |
|---|---|
| PDS | polydioxanone suture |
| PDO/MD | polydioxanone/morpholinedione |
| PDO/3MMD | polydioxanone/3-methyl-morpholine-dione |
| I.V. | inherent viscosity |
| Cryst. | crystallinity |
| Str. Stren. p.s.i. | straight tensile strength pounds per square inch |
| % Elong. | Percent elongation |
| Abs. % Rem./Days | Absorption % remaining/days |
| BSR % Rem./Days | Breaking strength retention % tensile strength remaining/Days |
| lb. Init. | pounds per square inch initially |
| N.T. | Not tested |
| $T_m$ °C. | crystalline melting point |

In order to determine the percentage in vivo absorption, two 2 cm segments of monofilament fiber having a diameter corresponding to size 4-0 suture are implanted aseptically into the left gluteal muscles of a number of female Long Evans rats. The implant sites are recovered periodically, such as, after periods of 5, 63, 120, 150 and 180 days and examined microscopically to determine the extent of absorption. A detailed test method is disclosed in U.S. Pat. No. 4,052,988.

In order to determine the in vivo tensile strength retention, segments of the sutures of several Examples are implanted in the posterior dorsal subcutis of female Long Evans rats for periods of 7, 14, 21 and 28 days. The sutures are recovered at the designated periods and tested for straight tensile strength with the results set forth in Table I.

The inherent viscosity readings are obtained for copolymer solutions in hexafluoro-2-propanol (1 g/l). The melting temperature ($T_m$) is obtained in nitrogen, using a D.S.C. (differential scanning calorimetry) apparatus. The percent crystallinity is determined by X-ray. Fiber tensile properties are measured on an Instron, Model No. 1122.

It will be noted from Table I that the polydioxanone control monofilaments require 182 days to be completely absorbed, in vivo, whereas the monofilaments of the present invention are completely absorbed, in vivo, in from 90 to 150 days, depending upon the sample considered and particularly, the fraction of the morpholinedione moieties in the chain molecules.

It is to be understood that inert additives such as coloring materials and plasticizers can be incorporated in the sutures of the present invention. Any of a variety of plasticizers such as, for instance, glyceryl triacetate, ethyl benzoate, diethyl phthalate, dibutyl phthalate and bis 2-methoxyethyl phthalate can be used if desired. The amount of plasticizer may vary from 1 to about 20 percent or more based on the weight of the polymer. Not only does the plasticizer render the filaments even more pliable, but it also helps in spinning. As used herein, the term "inert" means materials that are chemically inert to the copolymer, and biologically inert to living tissue.

Filaments of the present invention are adversely affected by moisture and are accordingly preferably packaged in a substantially moisture free environment and in hermetically sealed packages.

Filaments of the present invention may be used as monofilament or multifilament sutures, or may be woven, braided, or knitted either alone or in combination with absorbable fibers such as polyglycolide or poly (lactide-co-glycolide), or with nonabsorbable fibers such as nylon, polypropylene, polyethyleneterephthalate, or polytetrafluoroethylene to form multifilament sutures and tubular structures having use in the surgical repair of arteries, veins, ducts, asophagi and the like.

The relative proportions of absorbable filaments and non-absorbable filaments may be varied to obtain the absorption characteristics desired in the woven fabric or tubular implants. Methods of weaving and crimping vascular prostheses are described in U.S. Pat. No. 3,096,560.

Composite fabrics of absorbable and nonabsorbable materials fashioned by textile processes including weaving, knitting, and fabricating by the nonwoven felting of fibers are described in U.S. Pat. No. 3,108,357 and U.S. Pat. No. 3,463,158. Similar techniques may be used in the manufacture of surgical aids wherein nonabsorbable fibers are combined with absorbable fibers composed of the copolymers of this invention. The surgical utility of "bicomponent filaments" containing absorbable and non-absorbable components is described in U.S. Pat. No. 3,463,158, the teaching of which is incorporated herein by reference. Monofilaments of the copolymers of the present invention may be woven or knitted to form an absorbable fabric useful surgically in hernia repair and in supporting damaged liver, kidney, and other internal organs.

The products of the invention are useful in surgical applications where an absorbable aid or support is required, as for example, in the formation of surgical mesh, absorbable staples, artificial tendons, or cartilage material, and in other uses where a temporary aid during healing is needed. They may also be used to advantage in repairing hernias and in anchoring organs which have become loose.

The copolymers of the present invention are also useful in the manufacture of cast films and other solid surgical aids such as scleral buckling prostheses. Thus, cylindrical pins, clips, screws, reinforcing plates, etc., may be machined from the cast polymer having in vivo absorption characteristics depending upon the polymer composition and molecular weight.

Many different embodiments of this invention will be apparent to those skilled in the art and may be made without departing from the spirit and scope thereof. It is accordingly understood that this invention is not limited to the specific embodiments thereof except as defined in the appended claims.

We claim:

1. A copolymer, comprising a multiplicity of recurring A and B units, having the following general formula:

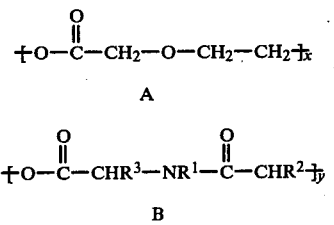

wherein x and y are integers, such that the A units comprise 85–99 mole percent, and the B units comprise 1–15 mole percent of the copolymer and $R^1$, $R^2$ and $R^3$ are each hydrogen or lower alkyl and may be the same or different.

2. The copolymer of claim 1, wherein each of $R^1$, $R^2$ and $R^3$ is hydrogen.

3. A copolymer, comprising a multiplicity of recurring A and B units having the following general formula:

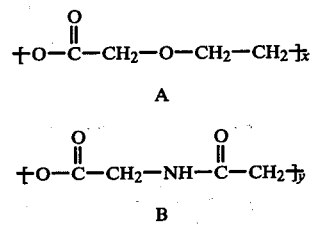

wherein x and y are integers, such that the A units comprise 94–98 mole percent, and the B units comprise 2–6 mole percent of the copolymer.

4. The copolymer of claim 3 wherein the A units comprise 95–97 mole percent, and the B units comprise 3–5 mole percent of the copolymer.

5. An absorbable surgical device formed from a copolymer, comprising a multiplicity of recurring A and B units, having the following general formula:

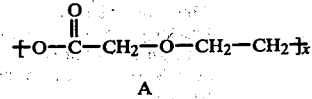

-continued

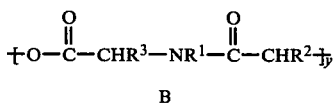
B wherein x and y are integers, such that the A units comprise 85–99 mole percent, and the B units comprise 1–15 mole percent of the copolymer and $R^1$, $R^2$, and $R^3$ are each hydrogen or lower alkyl and may be the same or different.

6. The device of claim 5, wherein each of $R^1$, $R^2$ and $R^3$ is hydrogen.

7. An absorbable surgical device, formed from a copolymer, comprising a multiplicity of recurring A and B units having the following general formula:

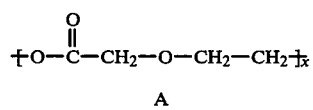
A

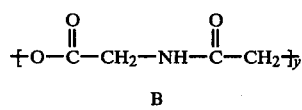
B wherein x and y are integers, such that the A units comprise 94–98 mole percent, and the B units comprise 2–6 mole percent of the copolymer.

8. The device of claim 7, wherein the A units comprise 95–97 mole percent, and the B units comprise 3–5 mole percent of the copolymer.

9. The device of claim 5, characterized by the fact that it is in the form of a filament.

10. The device of claim 9, in which the filament comprises a sterile suture.

11. The device of claim 10, in which the suture has a surgical needle attached to at least one end.

12. The device of claim 5, characterized by the fact that it is in the form of a clip.

13. A woven or knitted surgical fabric, comprised of filaments of claim 9.

14. A fabric of claim 13, in a seamless tubular construction.

15. A fibrillar surgical aid comprising knitted, woven or non-woven filaments of claim 9.

16. A surgical suture package, comprising a sterile enclosure and therein, a sterile filament of claim 10 having a surgical needle attached to at least one end.

17. A method of closing a wound by approximating and securing the wound tissue with the surgical filament of claim 9.

18. The copolymer of claim 1, prepared by copolymerizing p-dioxanone of the formula

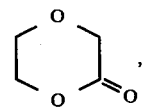

with a 2,5-morpholinedione of the formula

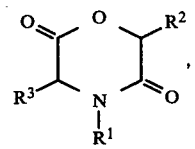

wherein $R^1$, $R^2$ and $R^3$ are as defined in claim 1.

* * * * *